United States Patent [19]
Payne, Jr. et al.

[11] Patent Number: 5,540,714
[45] Date of Patent: Jul. 30, 1996

[54] DISPOSABLE TOURNIQUET

[75] Inventors: C. Lee Payne, Jr.; John L. Lundberg, both of Atlanta, Ga.; J. Thomas Atkins, Scottsdale, Ariz.; Ray L. Hauser, Boulder, Colo.

[73] Assignee: Ingress Technologies, Inc., Phoenix, Ariz.

[21] Appl. No.: 986,455

[22] Filed: Dec. 7, 1992

Related U.S. Application Data

[63] Continuation-in-part of Ser. No. 812,045, Dec. 23, 1991, abandoned.

[51] Int. Cl.⁶ .................................................. A61B 17/12
[52] U.S. Cl. ......................................... 606/201; 606/203
[58] Field of Search ..................................... 606/201, 203

[56] References Cited

U.S. PATENT DOCUMENTS

| | | | |
|---|---|---|---|
| 3,628,536 | 12/1971 | Glesne | 128/327 |
| 3,930,506 | 1/1976 | Overend | 606/203 |
| 4,661,099 | 4/1987 | von Bittera et al. | 604/290 |
| 4,727,885 | 3/1988 | Ruff | 128/686 |
| 4,807,753 | 2/1989 | Goldstein | 206/390 |

*Primary Examiner*—John S. Hilten
*Attorney, Agent, or Firm*—Gregory J. Nelson

[57] ABSTRACT

A single-use disposable phlebotomy venous tourniquet formed from a strip of elastic fabric material. Such fabric may be initially selected or treated with a polymeric or elastomeric material to provide surfaces having predetermined frictional characteristics to minimize slippage and discomfort to the patient and to facilitate ease of use in knotting and releasing the tourniquet.

25 Claims, 2 Drawing Sheets

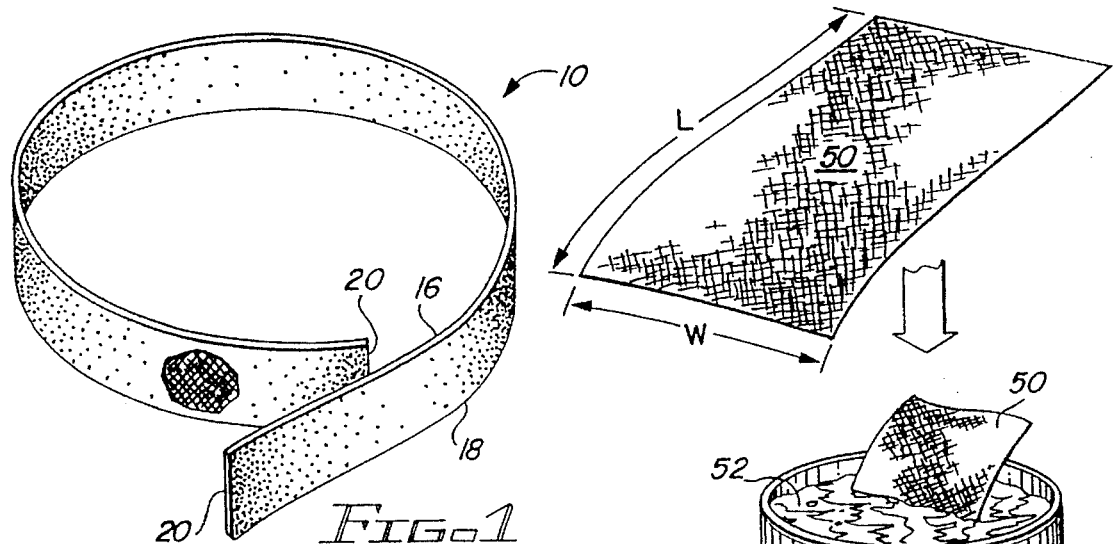
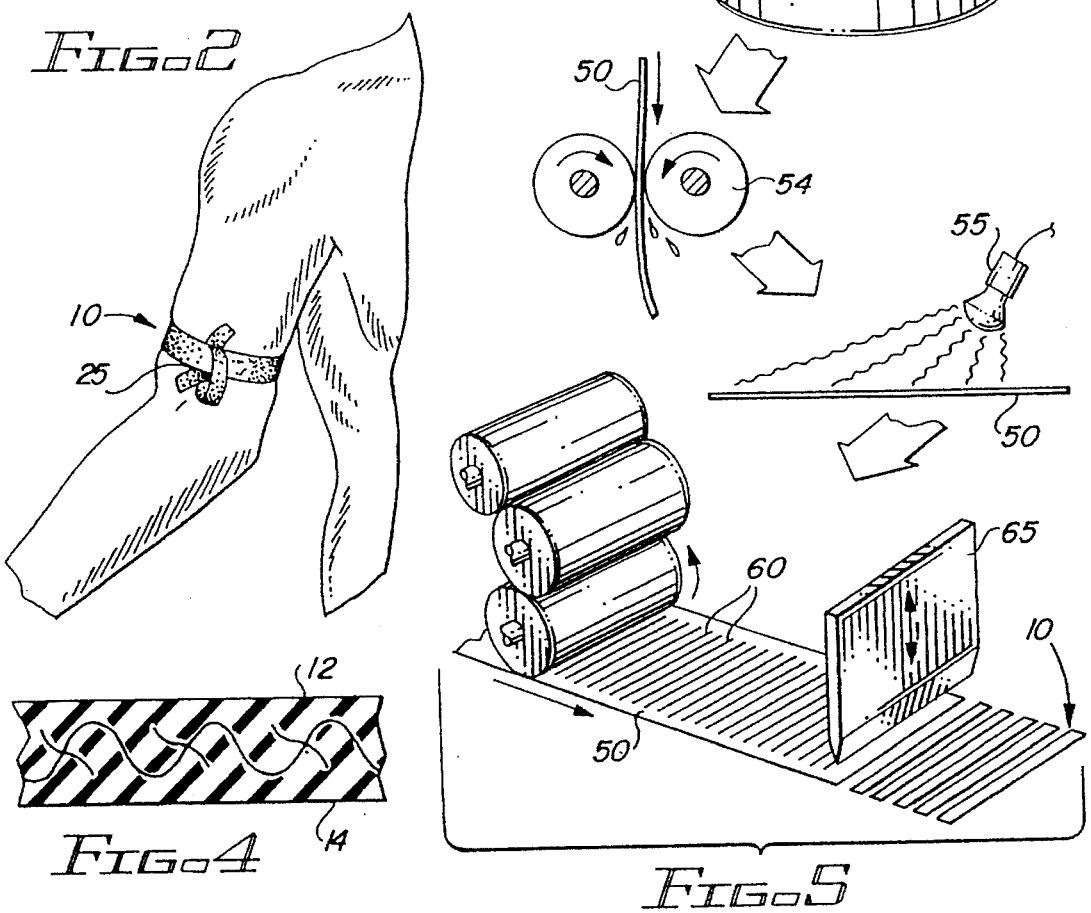

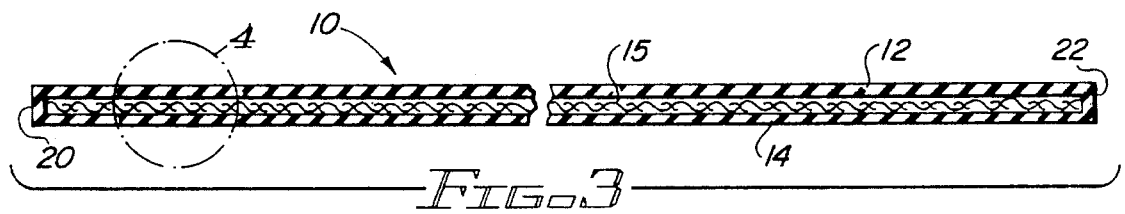
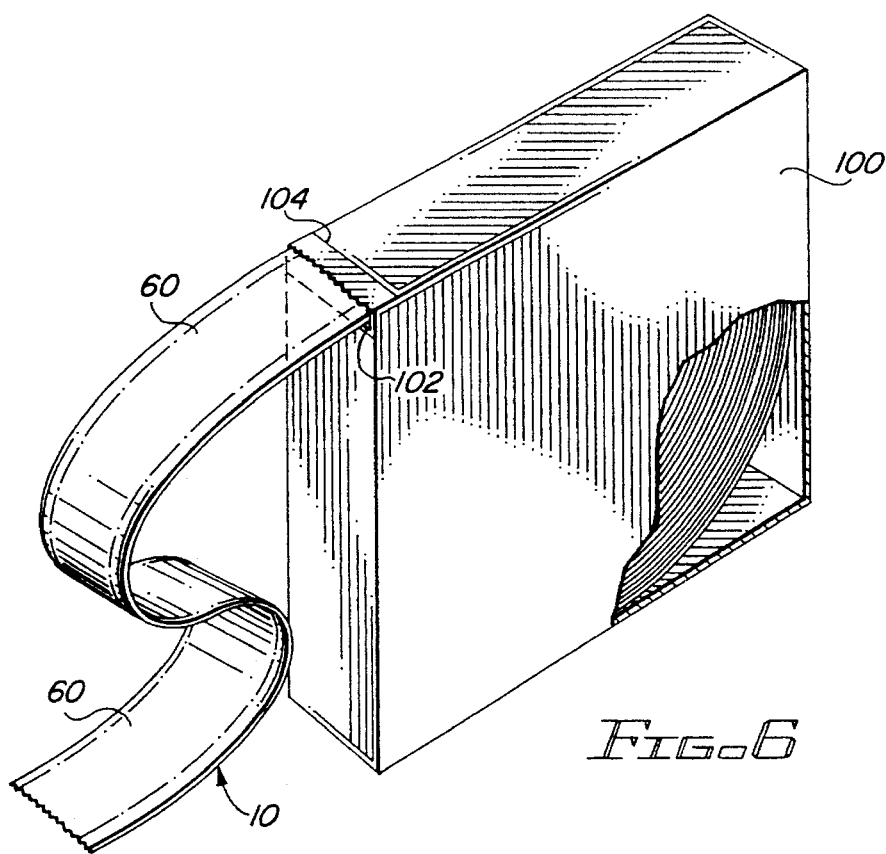

DISPOSABLE TOURNIQUET

This application is a continuation-in-part of abandoned U.S. patent application Ser. No. 07/812,045, filed Dec. 23, 1991, entitled "Disposable Tourniquet".

The present invention relates to a tourniquet and more particularly relates to a disposable tourniquet for phlebotomy and similar procedures for restricting venous blood flow to be used in lieu of conventional rubber tourniquets. The disposable tourniquet of the present invention minimizes discomfort to the patient and also reduces risk of transmission of infection to the patient, phlebotomist and other medical personnel.

Tourniquets are traditionally used in medical practice for restricting of blood flow or causing turgidity in veins. For example, when obtaining a blood sample, the medical technician or phlebotomist will normally place the tourniquet about the upper arm of the patient and apply pressure by tightening and knotting the tourniquet to induce turgidity in the veins in the lower arm. A length of rubber tubing or strapping is commonly used for this purpose. An appropriate venepuncture site is selected and the needle inserted, the blood sample removed and the needle withdrawn. Thereafter the rubber tubing or strap is removed usually by giving the tubing a quick pull to release the slip knot.

In the current state of the phlebotomy art, disposable syringes and needles are used and after use are discarded in an approved fashion in compliance with good medical practice and governmental regulations. The use of disposable items such as syringes, needles and latex gloves is practiced to guard against the spread of infectious vital and bacterial diseases. Such diseases include blood-borne viruses such as hepatitis B and acquired immune deficiency syndrome (AIDS). The medical profession is very aware of the risk of transmission of a blood-borne infection from patient to patient, from patient to medical attendant or from medical attendant to the patient. As indicated above, one way to guard against such transmission is the use of medical devices which are single-use devices which are disposed of after use. Disposable syringes, latex gloves, needles, bandages, gauze, cotton swabs, tapes and the like are routinely and mandatorily discarded after a single use to minimize the risk of transmission of infection.

Traditionally the one item in the phlebotomy procedure which is re-used is the latex rubber tourniquet which is used to cause turgidity in the veins and vessels. This necessary item is re-used and such re-use is inconsistent with the concerns about transfer of blood-borne pathogens. Accordingly, safe medical practice dictates the tourniquet should also be a single use device which is discarded after use. The latex rubber tourniquet also is objectionable because it pinches the patient's skin and pulls the body hair of the patient. The high stretchability (technically the low elastic modulus) of latex rubber causes localized pulling of body hair.

The conventional latex rubber tourniquet presents a particular problem when released as the resulting snapping action can result in the tourniquet contacting the venepuncture site and contaminating the device with blood. This disadvantage is also caused by the stretchiness of the rubber.

Accordingly, it is a principal object of the present invention to provide a disposable tourniquet which is effective, can be manufactured inexpensively and which will help avoid the possibility of contagion or transfer of infectious diseases.

Another object of the present invention is the provision of a disposable tourniquet which is more comfortable to the patient reducing pinching and pulling of the patient's skin and body hair.

A number of patents can be found in the prior art which show tourniquets of various construction. For example, U.S. Pat. No. 3,156,243 shows a tourniquet having an elongated central tubing portion of rubber and having opposite ends which may be frictionally engaged.

U.S. Pat. No. 3,910,280 discloses a tourniquet consisting of an elongate flexible tube with a rigid head at one end. The tube is placed about the body of the vessel with the free end engaged in locking apertures in the head which frictionally binds the outer surface of the tube. To prevent slippage of the tube, a second locking aperture may be provided.

U.S. Pat. No. 4,870,978 shows an adjustable tourniquet formed from a predetermined length of surgical elastomeric tubing which is doubled on itself and knotted along its length to form a series of loops terminating at a final knot. The device is positioned about a limb and the final knot is inserted through one of the loops to provide pressure on the limb.

U.S. Pat. No. 4,911,162 shows a tourniquet for restricting blood having a flexible, resilient, elongate member and a securing member at the end of the resilient member. The securing member has an aperture to receive the free end of the elongate member.

U.S. Pat. No. 3,628,536 shows a tourniquet formed from a strip of elastic material which has a series of spaced-apart apertures which may be selectively engaged in an upstanding projection or stud to hold the tourniquet tightened about the body member.

U.S. Pat. No. 3,930,506 shows a disposable tourniquet consisting of a flat, solid elastic band having a non-stretchable pressure sensitive strip member near the end. In use, a protective liner is peeled from the adhesive strip so the ends may be joined.

U.S. Pat. No. 4,273,130 shows a tourniquet having an elastic portion of fabric or plastic with a ring attached at one end. Velcro-type fasteners are provided so the free end may be looped through the ring to selectively tighten the tourniquet in place.

Other United States Patents of interest in this area are U.S. Pat. Nos. 4,661,099; 4,737,885; 4,566,436; 5,015,251; and 5,074,873.

Thus, while the prior art discloses various tourniquet arrangements, some of them disposable, they are of complicated designs which make them unsuitable for inexpensive manufacture. In today's medical economy, cost is a significant consideration, particularly with respect to the use of disposable devices. Further, many of the prior art tourniquets either have a surface which allows some slippage when positioned about the limb of a patient or a surface which will cause pinching or uncomfortable pulling of body hair when used.

Briefly, the present invention is directed to a single-use, disposable tourniquet for restricting venous blood flow which tourniquet is formed from a strip of elongate material which has predetermined elastic characteristics. The tourniquet may be fabricated from a single material composition or as a composite assembly of a material treated to provide a surface having predetermined characteristics. The material is selected from a variety of flexible, planar composite fabric materials such as woven, knitted or nonwoven fabric from natural or synthetic materials. In the composite embodiment, such fabric material is impregnated or coated with polymeric or elastomeric material to provide a surface having selected frictional characteristics so as not to slip when placed about the limb of a patient and which surface will also substantially minimize trauma to the patient by reducing the tendency of the tourniquet to pinch or pull body hair both when knotted and when released. The coating may be applied by various means such as by dipping, spraying or similar methods. In one preferred embodiment in which the material of the tourniquet is a composite material, a section of material is treated by coating or by impregnation with polymeric or elastomeric compositions to provide the desired surface characteristics. Either prior to or after treatment, appropriate messages may be imprinted on the material which may be either in the form of advertising or include use instructions. The tourniquets thereafter are individually formed by a slitting or cutting operation.

The above and other objects and advantages of the tourniquet of the present invention will be more fully appreciated from the following description, claims and drawings in which:

FIG. 1 is a perspective view of the disposable tourniquet according to the present invention;

FIG. 2 illustrates the application of the tourniquet to the arm of a patient.

FIG. 3 is a longitudinal cross sectional view of the tourniquet;

FIG. 4 is an enlarged detail view of a portion of the tourniquet as indicated in FIG. 3;

FIG. 5 illustrates the steps in the method of manufacturing the tourniquet according to the present invention; and FIG. 6 is a perspective view of a container for dispensing a roll of tourniquets.

While the present invention is described primarily as a phlebotomist's tourniquet, the present invention may be used for other applications such as vascular applications during surgical procedures.

Referring now to the drawings, particularly FIGS. 1, 3 and 5, the tourniquet of the present invention is generally designated by the numeral 10 and consists of an elongate strip of material which when finished has an upper surface 12, bottom surface 14, side edges 16 and 18 and opposite ends 20 and 22. The strip of material may be of various sizes but typically will be approximately ¾ " to 1½ wide and 12" to 24" in length after cutting and finishing. The strip may be fabricated from various materials, preferably woven, knitted or nonwoven cloth or fabric. The term "fabric" will be used throughout to designate the material of the strip and as used herein "fabric" means any material that is woven, knit, braided, or netted with any fiber; it may also be non-fibrous PVC, urethane, EVA copolymer or other elastomeric synthetic materials. The fabric can be formed from various fibers such as organic fibers such as cotton, animal fibers such as wool or may be synthetic or man-made such as cellulose fibers or synthesized fiber. The fabric may be one fiber or a combination of these fibers or without fibers. The primary characteristic is that the fabric material from which the tourniquet is formed be stretchable or elastic.

A primary advantage of the tourniquet of the present invention, in addition to disposability, is that in use it is less traumatic and is more comfortable to the patient. As discussed above, conventional latex rubber tourniquets will pinch the patient's skin or will tend to pull or tear at body hair, particularly when knotted and also when released. To minimize this undesirable characteristic, the fabric tourniquet of the present invention is suitably treated to provide surfaces 12 and 14 with predetermined frictional characteristics. Preferably the surface treatment is transparent to permit imprinting and is also flexible so that the surface will stretch along with the fabric substrate. Opposite surfaces 12 and 14 are both treated to provide reversibility so either surface may be placed against the patient's body when the tourniquet is used.

The selected coating may be variously applied as the tourniquet material may be sprayed or dipped in an aqueous dispersion or solution and thereafter processing may include squeezing, kiss rolling or knife edge coating. The coating may also be applied by a hot melt process. Preferable coatings are polymeric resins or elastomeric materials with a glass transition temperature which is not greater than about 50° C. Acceptable coatings include elastomeric or polymeric solutions such as acrylics, rubber, latex, latex polymerics, urethane, ethylene vinyl acetate (EVA) and polymeric vinyl chloride (PVC). The coatings may be applied from water emulsions, plastisol dispersions or solvent based emulsion.

Referring to FIG. 5, the tourniquet of the present invention is disposable and therefore medical economics dictate that it must be inexpensive to manufacture to make it suitable for single use medical applications. To fabricate the individual tourniquet, a section of material 50 as shown in FIG. 5 is selected. The selected fabric material will have the characteristics described above having the requisite elasticity. The material may be a natural occurring or synthetic fibers or a mixture of fibers as indicated above. The section of material is cut to the desired length "L". The width "W" is selected so that a predetermined number of individual strips can be cut from the section of material. After the section of material 50 has been selected, it is first treated to obtain the desired surface characteristics. As shown, the material is impregnated, coated or surface treated with a polymeric resinous or elastomeric material. Preferably, the material is dipped into a liquid coating dispersion or solution 52 and thereafter squeezed by rollers 54 to remove excess liquid. Drying is accomplished by heating using a heater 54 such as a drum dryer, a microwave heater, hot air ovens or, as shown, by exposure to an infrared heat source 55. After the material has been treated and dried, at least one surface 12, 14 of the material is provided with appropriate imprinted message 60 by offset, silk screen or other printing techniques. The imprinted message 60 may include brand name, manufacture and any special instructions for use.

After printing, individual tourniquets are cut from the larger section of starting material 50 using a die cutter 65 to yield a plurality of individual tourniquets 10 which can then be suitably packaged for distribution. The die cutter may be a drum type "bologna-cutter" which has a plurality of circular cutting edges which will simultaneously cut a plurality of strips. Packaging may be in clear, non-sterile sealed packages 70 of poly film having a tear strip 75 for convenience.

In order to establish the efficacy of the present invention, disposable tourniquets were made in the following manner. Each tourniquet consisted of a strip of approximately ¾" in width and 18" in length of a flexible, planar, composite material which has been found suitable for most applications. Other sizes for special applications may be provided. A particularly suitable material is a stretch fabric which is a double-knitted cotton sold under the brand name "Spandex". The fabric selected had a weight of 8 ounces per square yard. The stretch fabric was coated with a copolymer of polyvinylidene chloride with a glass transition temperature of about 22° C. The coating was applied by dipping the material in a polymer latex. The coated material was allowed to air dry and thereafter heated for about 30 to 45 minutes at a temperature of between 85° C. to 105° C. to flow the dried latex to form films on the yarn and the fabric. Coating weights were from about 8% to 31% by weight.

Another method of manufacture involves providing a synthetic starting material such as PVC, urethane, polyurethane, EVA copolymer, or the material sold under the designation "Fiberweb". This material is initially in sheet film typically 30"–48" in width and having a thickness of from about 6–12 mil. The material is selected to have the desired elasticity with a modulus of elasticity in the range of approximately 1.0 to 4.4 pounds of force at 10% elongation and having a coefficient of friction to itself of about 0.45 to 1.5.

The film is serially slit into tape-like strips of selected widths, typically ¾" to 1½". The tape is then repetitively printed with appropriate indicia and information such as manufacturer identification and instructions regarding use. The tape strips are perforated at predetermined intervals, as for example every 18". As shown in FIG. 6, the strips are then either packaged singly in a suitable manner such as in a clear poly bag or are rolled and contained in a box with a dispensing slot to allow the perforated tourniquet to be separated individually. The strips may be rolled unperforated and contained in a box 100 with a dispenser slot 102 and cutter 104 to facilitate withdrawing and severing a single tourniquet of variable length at the time of use.

The methods of manufacture of material described above provide tourniquet strips that can be effectively manufactured at an acceptable cost. The resulting products had the desired elasticity and the frictional characteristics of the surface provided substantial advantages over prior art tourniquets. When a tourniquet as described above is placed about the limb of a patient and tightened by knotting as shown in FIG. 2, the knot 25 was easily formed and stayed in place without slipping. The knotting procedure did not tend to pinch the patient or pull hair in a manner uncomfortable to the patient as was common with conventional tourniquets. Similarly, tourniquet release was easily achieved by pulling the knot to untie it.

Because of the design, the tourniquet is easily released after completion of the phlebotomy procedure and may be conveniently disposed of as by incineration preventing transfer of infection between patients or medical attendants. Conventional tourniquets which are re-used present a particular problem when released as the resulting snapping action can result in the tourniquet contacting the venepuncture site.

As indicated above, non-composite disposable tourniquets have also been made at lower cost than the composite products using materials with especially selected friction and stretch characteristics. Tests were made with plastic and elastomeric films comparing their physical characteristics and their performance as tourniquets as noted in Table 3. The static friction coefficient of a material to itself was noted to be a significant factor in the ability of the tourniquet to hold a knot. In some cases, the friction coefficient was so high that a knotted tourniquet would not release its slip knot easily.

This stretch of tourniquets was tested with a number of conventional and novel materials and it was noted that effective tourniquet performance was obtained when the material was stretched 15 to 64%. The more stretchy (lower modulus) latex tourniquets performed effectively in the range of 20 to 64% and the more plastic (less stretchy) material performed well with stretch in the range of 15 to 33%. The more plastic, higher modulus materials such as EVA copolymer, PVC film, and urethane derivatives were observed to cause little or no pulling of body hair or pinching of skin when used as a tourniquet.

The stiffness of different plastic and elastomeric films were tested, as noted in Table 5. The stress relaxation was also tested for these materials to learn the amount of force maintained over a time period of two minutes. Table 5 presents the stress relaxation as percent force decay in 2 minutes.

Tables 1, 2 and 3 set forth preferred physical characteristics and preferred tourniquet fabrics.

Tables 4 and 5 provide criteria for selecting disposable tourniquet material with attributes of low cost, knot-holding ability, knot-releasing ability, restriction of blood flow, and avoidance of hair pulling characteristics. Thus, from the tables it may be concluded that a disposable tourniquet for restricting blood flow comprising an elongate strip of plastic, elastomeric or composite fabric material should having the following characteristics: force at 10% elongation exceeding 1 pound/inch width; force decrease during 2 minutes of stretch at 10% elongation not more than 15% of the initial force; and having friction coefficient to itself in the range of 0.45 to 1.5. The modulus of elasticity should be about 1.0 to 4.4 pounds of force at 10% elongation. The material should also be incineratable under EPA and other applicable safety and environmental standards.

TABLE 1

Preferred Characteristics of Tourniquet Fabric

| I. PHYSICAL | II. CHEMICAL |
| --- | --- |
| 1. Density (Specific Gravity) 1.0+ | Behavior Toward: (a) Acids - Resistant |
| 2. Moisture Swelling - Low | (b) Alkalies - Resistant (c) Dyes - Printable |
| 3 Stress-Strain Behavior (a) Strength - 0.5+ (b) Elongation - 5 to 50% @ Tensile Load 1# to 10# (c) Stiffness - Moderate (d) Toughness - Good (e) Elasticity - Good (f) Resilience - Good | (d) Solvents - Not Appreciably Affected |
| 4. May be incinerated under EPA and other applicable health, envorornmental and safety standards. | |

TABLE 2

Examples Of Fabrics That Are Acceptable:

| Natural | Man-Made | Synthesized | |
| --- | --- | --- | --- |
| Silk | Cellulose (Paper) | Acrylic | Azlon |
| Wool | Rayon | Anidex | Nylon |
| Cotton | Acetate | Aramid | Nytril |
| | Triacetate | Lastrile | Olefin |
| | | Modacrylic | Saran |
| | | Novoloid | Vinyl |
| | | Polyester | Vinyon |
| | | Spandex | |
| | | Synthetic Rubber | |

TABLE 3

Examples of Elastomeric/Polymeric Synthetic Fabrics That Are Acceptable

| PVC | EVA Copolymer |
| --- | --- |
| Urethane | Fiberweb |
| Polyurethane | |

TABLE 4

Friction and Knot Characteristics of Selected Materials

| Material | Friction Coefficient | Holds Knot | Unties Easily |
| --- | --- | --- | --- |
| Latex rubber strip | 0.66 | Yes | Yes |
| PVC film #1 | 2.51 | Yes | No |
| PVC film #2 | 3.24 | Yes | No |

TABLE 4-continued

Friction and Knot Characteristics of Selected Materials

| Material | Friction Coefficient | Holds Knot | Unties Easily |
| --- | --- | --- | --- |
| Urethane PS3110S | 0.31 | No | — |
| Urethane PS7010 | 0.47 | Yes | Yes |
| Urethane MP1495 | 1.56 | Yes | No |
| EVA copolymer | 0.77 | Yes | Yes |
| Fiberweb 30 | 0.44 | No | — |
| Cotton Fabric | 0.43 | Yes | Yes |

TABLE 5

Stiffness and Stress Relaxation of Tourniquet Materials
all strip materials 1" wide

| Material | Force, lb., at Elongation of | | Force decay in 2 minutes at 10% elongation, lb. |
| --- | --- | --- | --- |
|  | 10% | 20% |  |
| Latex Rubber | 0.50 | 0.86 | 0.02 |
| Latex Tubing I | 0.61 | 1.06 | 0.02 |
| Latex Tubing II | 0.26 | 0.45 | 0.01 |
| PVC Film II | 1.30 | 2.55 | 0.02 |
| Urethane PS7010 | 2.11 | 3.23 | 0.14 |
| EVA Copolymer (ethylene vinyl acetate) | 3.52 | 4.36 | 0.30 |

It will be obvious from the foregoing that the present invention provides an effective, inexpensive and medically acceptable tourniquet which when properly used will lessen the possibility of transfer of blood-borne pathogens.

The tourniquet of the present invention can be easily manufactured, employed for single use and thereafter disposed of by incineration. The tourniquet is more comfortable for the patient.

It will be obvious to those skilled in the art to make various changes, alterations and modifications to the disposable tourniquet described herein. To the extent such changes, alterations and modifications do not depart from the spirit and scope of the appended claims, they are intended to be encompassed therein.

We claim:

1. A disposable tourniquet for restricting venous blood flow during phlebotomy procedures comprising:
   (a) an elongate strip of fabric material having elastic characteristics;
   (b) said strip of fabric material being treated with a coating selected from the group consisting of elastomeric solutions, polymer solutions, acrylics, rubber latex, latex polymers, urethane, ethylene vinyl acetate and polymeric vinyl chloride; and
   (c) wherein said coating has a glass transition temperature of about 22° C.

2. The tourniquet of claim 1 wherein said material is a knitted cotton material.

3. The tourniquet of claim 1 wherein said fabric material is selected from the group consisting of polyurethane and urethane derivatives.

4. The tourniquet of claim 1 wherein said material is non-composite, non-fibrous, synthetic material having a coefficient of friction of itself in the range of about 0.45 to 1.5 and elasticity in the range of about 1.0 to 4.4 pounds of force at 10% elongation in which the forces at 10% elongation exceeds one pound/inch width.

5. The tourniquet of claim 1 wherein said strip is printed with information.

6. The tourniquet of claim 1 wherein said strips are cut into predetermined lengths and packaged.

7. The tourniquet of claim 1 wherein said strip is perforated at predetermined intervals and provided for use in a dispenser.

8. The tourniquet of claim 1 wherein said strip is provided in a dispenser with a cutter whereby predetermined portions of the strip may be selectively severed for use.

9. The tourniquet of claim 1 wherein the fabric material is a coated knitted fabric.

10. The tourniquet of claim 1 wherein said fabric material is a woven material textile.

11. The tourniquet of claim 1 wherein said fabric material is a non-woven material textile.

12. The tourniquet of claim 1 wherein said fabric material is a woven synthetic textile.

13. The tourniquet of claim 1 wherein said fabric material is a non-woven synthetic textile.

14. A disposable tourniquet for restricting venous blood flow comprising:
   (a) an elongate strip of ethylene vinyl acetate (EVA) of predetermined width having opposite surfaces and opposite ends, said strip having predetermined elastic characteristics in which the force required for 10% elongation exceeds one pound/inch width and the force decrease during two minutes of stretch at 10% elongation does not substantially exceed 15% of an initial applied force and wherein said strip has a friction coefficient to itself in the range substantially between 0.45 to 1.5.

15. The tourniquet of claim 14 wherein said strip is printed with information.

16. The tourniquet of claim 14 wherein said strips are cut into predetermined lengths and packaged.

17. The tourniquet of claim 14 wherein said strip is perforated at predetermined intervals and provided for use in a dispenser.

18. The tourniquet of claim 14 wherein said strip is provided in a dispenser with a cutter whereby predetermined portions of the strip may be selectively severed for use.

19. A disposable tourniquet for restricting venous blood flow comprising an elongate strip of coated synthetic material of predetermined width having opposite surfaces and opposite ends, said strip having predetermined elastic characteristics in which the force required for 10% elongation exceeds one pound/inch width and the force decrease during two minutes of stretch at 10% elongation does not substantially exceed 15% of an initial applied force and wherein said strip has a friction coefficient to itself in the range substantially between 0.45 to 1.5.

20. The tourniquet of claim 19 wherein the fabric material is spandex.

21. The tourniquet of claim 19 wherein the fabric material is polyester.

22. The tourniquet of claim 19 wherein said strip is printed with information.

23. The tourniquet of claim 19 wherein said strips are cut into predetermined lengths and packaged.

24. The tourniquet of claim 19 wherein said strip is perforated at predetermined intervals and provided for use in a dispenser.

25. The tourniquet of claim 19 wherein said strip is provided in a dispenser with a cutter whereby predetermined portions of the strip may be selectively severed for use.

* * * * *